United States Patent [19]

Johnston et al.

[11] Patent Number: 4,743,673

[45] Date of Patent: May 10, 1988

[54] HYDROPHILIC CARBOXY POLYURETHANES

[75] Inventors: Christian W. Johnston; John M. Teffenhart, both of Neshanic Station, N.J.

[73] Assignee: Tyndale Plains-Hunter, Ltd., Princeton, N.J.

[21] Appl. No.: 944,667

[22] Filed: Dec. 19, 1986

[51] Int. Cl.$^4$ .............................................. C08G 18/30
[52] U.S. Cl. ...................... 528/60; 428/425; 428/423.1; 528/64; 528/66; 528/71; 528/72; 252/182.22
[58] Field of Search ................... 428/425; 528/60, 64, 528/66, 71, 72

[56] References Cited

U.S. PATENT DOCUMENTS 4,156,067 5/1979 Gould .................................. 528/73

*Primary Examiner*—Maurice J. Welsh
*Assistant Examiner*—Sam A. Acquah
*Attorney, Agent, or Firm*—Ratner & Prestia

[57] ABSTRACT

Hydrophilic polyurethane polymers having carboxy groups in the polymer backbone are prepared by reacting a polyol component, an ester of a carboxylic acid and a polyisocyanate to form a polyurethane intermediate. The intermediate is then saponified and the saponified product neutralized to form free carboxy groups. The water absorption of the intermediates and saponified polymers is above 10% and the polyurethanes may range from rigid solids to gel-like, high water absorptive polymers. Neutralization of the carboxy group with ammonium hydroxide produces a water soluble polyurethane which becomes water insoluble when the ammonia is driven off. The carboxy groups introduced into the polymeric chain provide reactive sites for attachment of various side-groups and also allow for various curing procedures. The polymers exhibit excellent adhesion to various substrates, and are suitable for use as light sensitive photographic layers on films, paper or glass; as boat and pipe coatings for decreasing hydrodynamic drag; as drug delivery systems; as burn and wound dressings; in cosmetic applications; in body implants; as coatings on cannulae; and a host of other applications.

37 Claims, No Drawings

HYDROPHILIC CARBOXY POLYURETHANES

TECHNICAL FIELD

This invention relates to hydrophilic polyurethane polymers modified to contain carboxy groups in the polymer backbone, to processes for preparing the so-modified polyurethanes, and to uses thereof.

BACKGROUND OF THE INVENTION

Numerous polymer systems that contain free carboxy groups are known in the art. It is difficult, however, to prepare a carboxy polyurethane, that is, a polyurethane having free carboxyl groups, because isocyanate, which is a necessary component in the preparation of any polyurethane, is quite reactive with the carboxyl groups of the carboxylic acid reactants used to introduce the carboxyl group.

One approach to the introduction of carboxy groups into a polyurethane resin chain is described in U.S. Pat. No. 3,412,054 to Milligan et al. In that patent, a 2,2-di(-hydroxymethyl)alkanoic acid is reacted with an organic diisocyanate to produce a polyurethane containing unreacted carboxylic acid groups. These acids are unique because their carboxyl groups do not react to any significant extent with the isocyanates to prevent the formation of the desired carboxy resin. However, very few carboxylic acids have this character, thus reducing the cost effectiveness of this approach.

Another approach is that of U.S. Pat. Nos. 4,156,066 and 4,156,067 to Gould. In these patents, a polyfunctional lactone, preferably containing at least three hydroxyl groups, is reacted with an isocyanate and one or more diols to form a polyurethane having lactone groups in the polymer backbone. Upon saponification or hydrolysis the lactone rings open up to form carboxyl groups. However, the amount of carboxyl which can be introduced via the lactones is limited such that the enhancement of properties attributable to the carboxyl groups, e.g., water-solubility, cross-linkability or other reactivity characteristic of carboxyl functionality, is marginal for some applications.

SUMMARY OF THE INVENTION

It has now been found that hydrophilic polyurethanes which contain carboxy (carboxylic acid or carboxylate, i.e., salt) groups in the polymer backbone can be prepared from carboxylic acids, the carboxyl functionality of which would normally be lost by reaction with organic isocyanate, by esterifying the carboxyl functionality prior to reaction with the isocyanate. This shields the carboxyl groups to prevent reaction with the isocyanate. Once the polyurethane is formed, the ester groups are easily converted to carboxylate (salt) groups by saponification with a suitable base, and to free carboxyl (acid) groups by neutralization of the saponified polymer with a suitable acid. The carboxylic acid ester reactants must also contain active hydrogen containing groups as sites for reaction with the isocyanate for urethane formation. As is known, active hydrogen groups include hydroxyl (in an aliphatic or aromatic moiety), mercaptan, oxime, amido, amino (primary or secondary), hydrazine, and the like.

The shielding afforded by the ester groups permits use of a wide variety of carboxylic acids (as contrasted with the limited class of U.S. Pat. No. 3,412,054), including acids having a plurality of carboxyl groups and other functional groups, and thus opens up opportunity for substantial enhancement of properties attributable to higher amounts of carboxyl functionality, particularly adhesion to polar and/or polarizable substrates and the preparation of resins with differing pH and susceptibility to crosslinking.

More particularly, the carboxy functionality of the polyurethanes supplements their hydrophilicity by providing reactive sites for introduction into the polymer of a variety of other groups, by facilitating chemical curing of films, coatings and other products prepared from the polyurethanes, and by improving adhesion to different types of substrates. The hydrophilic carboxy polyurethanes typically are low melting solids, flowing in the range of about 90° C. to 250° C., and can be used as coatings or can be fabricated into a wide variety of shaped bodies including films and cannulae using conventional thermoplastic polymer processing procedures. The polyurethane ester intermediate is soluble in lower aliphatic alcohols, chlorinated solvents, esters, aromatic solvents and a host of other polar and non-polar solvents, but insoluble in water. The saponified polymer is partially soluble in lower aliphatic alcohols, particularly if water is present, and soluble in water if sufficiently modified.

Accordingly, in one aspect of the invention, carboxy groups are incorporated into polyurethanes by esterifying the carboxyl group or groups of a carboxylic acid having other active hydrogens for reaction with organic isocyanate, and reacting the esters in the presence of a polyol component with an organic isocyanate to form a polyurethane intermediate. Alternatively, a prepolymer can be formed by reaction of the ester and isocyanate, and polyurethane is then produced by reaction of the prepolymer with polyols. By appropriate selection of the polyol component and control of the ratio of isocyanate (NCO) to active hydrogen in the reaction mixture, the resulting polyurethane intermediate polymer is hydrophilic as evidenced by its ability to absorb water to at least 10% of its weight, preferably about 20% to 200%.

In other aspects of the invention, the ester groups of the hydrophilic polyurethane intermediate are saponified by reaction with an aqueous base and the saponified groups are neutralized to form free carboxyl groups, thereby making the carboxyl groups available for reaction with other functional groups or for improved chemical curing or adhesion.

In still other aspects of the invention, the hydrophilic carboxy polyurethanes prepared in the manner described above are used in light sensitive photographic layers on films, paper or glass, in boat and pipe coatings for decreasing hydrodynamic drag, as drug delivery systems, as burn and wound dressings, in cosmetic applications, in body implants and catheters, as coatings on cannulae, and in a host of other applications where the hydrophilic character and carboxy functionality are useful properties. In general, the polyurethanes can be used in any of the applications described in the above-cited U.S. patents but with less complicated processing such as the need, in the case of the lactone-containing polyurethanes, of removing unreacted lactone.

DETAILED DESCRIPTION

The polyurethanes of the present invention are prepared by the reaction of:
(A) a polyol component comprising at least one of
    (a) an alkylene glycol, (b) a long chain polyoxyalkylene glycol, and
(c) a linear polyester diol derived from the condensation of one or more diols with one or more dibasic acids;
(B) a carboxylic acid ester component comprising at least one of
(a) a hydroxy carboxylic acid ester selected from at least one of

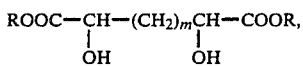

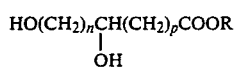

and

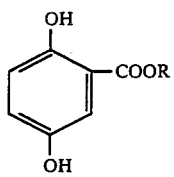

wherein R is an aliphatic group; m and p independently are integers of from 0 to 12 and n is an integer of from 1 to 12; and
(b) an amino acid ester having at least two active hydrogen atoms; and
(C) an organic isocyanate or isocyanate precursor containing at least two NCO groups;
the ratio of NCO to active hydrogen atoms in the reaction mixture being from 0.5/1 to 1/1, preferably about 0.7/1 to 0.95/1.

The polyol component (A) generally comprises one or more water soluble glycols having a molecular weight of at least about 50, preferably at least about 200, more preferably about 1000 to 8000 or more, and may be derived from simple alkylene glycols, long chain polyoxyalkylene glycols, and esters or ether-ester block-containing diol resins. Representative alkylene glycols (a) include the low molecular weight glycols and glycol ethers such as ethylene glycol, propylene glycol, diethylene glycol, dipropylene glycol, triethylene glycol, and the like. Suitable long chain polyoxyalkylene glycols (b) consist predominantly of oxyethylene or oxypropylene groups, though a minor proportion of other oxyalkylene groups may be included, having a number average molecular weight of from about 400 to 20,000. Block copolymer polyols obtained by adding ethylene oxide to a polyoxypropylene chain are also useful.

Representative linear polyester diols (c) are derived from the condensation of one or more alkylene glycols with one or more dibasic acids and include reaction products of x moles of a difunctional acid such as adipic, sabacic, dimeric acid, phthalic and maleic etc., and x+1 moles of difunctional linear glycols such as ethylene glycol, polyethylene glycols (molecular weight 100-600, preferably 200-300), propylene glycol, polypropylene glycols (molecular weight 100-600, preferably 200-300), 1,4-butane diol, polybutylene glycols (under 400 molecular weight) and the like. Mixtures of acids and/or glycols may be used and the value of x may vary from 1 to about 10. The molecular weight increases as x increases, the preferred value of x being 3-6. However, the molecular weight should not so high that the ester portion becomes the major portion of the polymer, an undesirable result due to the hydrophobic character of ester groups.

A minor portion (10 wt. % or less, preferably about 2 wt.% or less) of the polyol component (A) may comprise polyols having three or more hydroxyl groups, such as glycerol or sorbitol, provided the type and amount of the polyol does not cause undue and/or premature crosslinking of the polyurethane.

R in the above formulas and the ester group of the amino acids typically is an alkyl or alkenyl group containing 1 to about 12 carbon atoms or more, in some cases preferably at least 4 carbon atoms, e.g., 4 to 8 carbon atoms, for the reason explained in Example 1 below.

Representative carboxylic acid esters of (B) are hydroxy mono carboxylic acid esters such as glyceric acids esters including D-ethyl glycerate and D-methyl glycerate; trihydroxy n-butyric acid esters such as D-methyl erythronate; dihydroxy benzoic acid esters such as methyl or ethyl 3,4-dihydroxybenzoate, methyl or ethyl 2,4-dihydroxybenzoate, methyl or ethyl 2,5-dihydroxybenzoate, methyl or ethyl 3,5-dihydroxybenzoate and methyl or ethyl 2,6-dihydroxy-4-methylbenzoate; and hydroxy dicarboxylic acid esters such as methyl or ethyl dihydroxymalonate, dimethyl or diethyl bis(hydroxymethyl)malonate, dimethyltartarate, diethyltartarate, dibutyltartarate, and the like, including isomers thereof. Representative amino acids which may be esterified to form amino acid esters (b) are mono amino acids such as DL serine, glycine, alanine, valine, leucine and the like; amino derivatives of dibasic acids, such as aspartic acid, glutamic acid and the like, and polyamino acids such as L-lysine and arginine. The amino groups may be positioned anywhere on the carbon chain of the acid and thus include alpha, beta, gamma and delta amino acids.

The foregoing and a host of other carboxylic acids which may be esterified to form component (B) of the reaction mixture are described in *Organic Chemistry* by F. C. Whitmore, second edition, Dover Publications (1961), pages 348-350, 397-404, and 497-522, incorporated herein by reference, and in other standard tests. It will be evident from the literature that the esters may carry other active hydrogen-containing groups along with or in place of hydroxyl and/or amino, such as mercapto groups. The esters may be used singly or in mixtures of two or more, including combinations of esters (a) and (b) of component (B). The type (a) esters are preferred, either as single esters or as any mixtures thereof.

The organic isocyanate used in the present invention may be represented by $R(NCO)_q$ wherein q is an integer greater than 1, preferably 2-4, and R is an aliphatic, alicyclic, aliphatic-alicyclic, aromatic, or aliphatic-aromatic hydrocarbon compound of from 4 to 26 carbon atoms, but more conventionally from 6 to 20 and preferably from 6 to 13 carbon atoms. Representative isocyanates are: tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate, cyclohexylene 1,4-diisocyanate; the aromatic isocyanates such as 2,4- and 2,6-tolylene diisocyanate, 4,4-diphenylmethane diisocyanate, 1,5-naphthalene diisocyanate, dianisidine diisocyanate, tolidine diisocyanate, m-xylylene diisocyanate, tetrahydronaphthalene-1,5 diisocyanate and neopentyl tetra isocyanate.

The preferred isocyanate is methylene bis(cyclohexyl-4-isocyanate) sold by Mobay Chemical Corp. under the trademark "DESMODUR W." Other somewhat less preferred isocyanates are trimethyl hexamethylene diisocyanate and isophorone diisocyanate.

Other compounds which are useful are organic isocyanate equivalents which produce urethane linkages such as the nitrile carbonates, i.e., the adiponitrile carbonate of the formula:

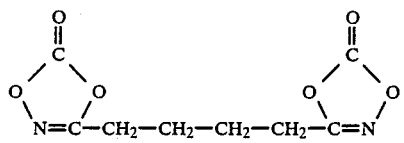

The proportions in which the polyols (A) are used, particularly the preferred combination of a long chain polyoxyalkylene glycol and a low molecular weight alkylene glycol, e.g., diethylene glycol, depend on the hydrophobic-hydrophilic balance desired in the final product. Increasing the molecular weight of the long chain polyoxyalkylene glycol and/or the amount of this component, for example, contributes strong hydrophilic properties to the final product. This effect may be counter-balanced by increasing the proportion of low molecular weight alkylene glycol, i.e., diethylene glycol or dipropylene glycol.

Thus, because the number of polyalkylene oxide groups in the polyurethane primarily determines hydrophilic properties, it is a simple matter to choose mixtures of reactants such that the final product will have the desired hydrophilicity and other properties. By choosing the molecular weight of a polyol or by using two polyols of different molecular weight, one may "tailor make" products having a wide range of properties. Other modifications of the hydrophilic polyurethane polymers may be made by adding a dialkanol tertiary amine such as diethanol methyl amine to the reaction mixture. The foregoing and other considerations relating to selection of polyol components for obtaining hydrophilic character is well known in the art, as described in U.S. Pat. Nos. 3,822,238, 3,975,350, 4,156,066 and 4,156,067, incorporated herein by reference.

In one method of making the polyurethane resins of this invention, a homogeneous mixture of the polyol component and water is prepared and the organic isocyanate is reacted with the mixture. In another method or preparation, a prepolymer may first be formed by reaction of the organic isocyanate and ester, followed by reaction with the polyol components. In either case the urethane-forming reaction may be catalyzed by a known catalyst for such reaction, suitable ones being tin salts and organo tin esters such as stannous octoate and dibutyl tin dilaurate, tertiary amines such as triethyl diamine (DABCO), N,N,N',N'-tetramethyl-1,3-butane diamine and other recognized catalysts for urethane reactions, with care being taken not to heat the reaction mixture unduly since undesirably dense crosslinking may result.

Water in the reaction mixture causes evolution of carbon dioxide, resulting in the polymer being obtained as a foam. This is an advantage in that the foamed polymer, owing to its large surface area, exhibits a high rate of dissolution, thereby facilitating the preparation of solutions of the polymer. In adding the requisite quantity of water to the reaction mixture, allowance should be made for any moisture that may be present in the glycol components. It is not unusual for commercial grades of alkylene glycols and polyoxyalkylene glycols to contain varying amounts of water. Moreover, such glycols tend to be hygroscopic and even if free of water, may become contaminated with moisture from atmospheric exposure. Preferably, however, sufficient water will be present or added to cause foaming of the polyurethane polymer as it is formed. Generally, trace amounts up to about 0.5 parts by weight of water based on 100 parts by weight of the total reaction mixture (exclusive of catalyst) will be effective, and for foaming, from about 0.1 to about 0.5 part by weight on the same basis.

Upon completion of the reaction of the polyol component, ester and polyisocyanate, the polyurethane resin intermediate may be dissolved in an appropriate solvent, e.g., methanol, and saponified with a strong aqueous base such as an alkali metal hydroxide, e.g., sodium or potassium hydroxide, while heating at reflux temperature for about 30–60 minutes. The resulting carboxylate polymer may be used directly in many of the applications described below or may be neutralized with an acidic material to a low pH (e.g., pH 3), preferably using a mineral acid such as dilute hydrochloric acid, to form carboxyl groups. Under ambient or normal conditions of polymer formation, the carboxyl groups can react with the urethane groups of the polymer to form loose or light crosslinks comprising ester or salt groups. If the polymer is heated sufficiently (as in a molding operation), the carboxyl groups themselves can interact to cause tight, dense crosslinking, probably by elimination of water, rendering the polymer insoluble in solvents in which non-carboxyl group containing polyurethanes are soluble.

Upon neutralization of the carboxyl-containing polyurethane with ammonium hydroxide, the polymer will become water soluble so long as it is not heated to a high temperature. If thus heated or cast from solution, ammonia will be driven off, leaving a water insoluble film.

The carboxyl groups also provide sites for light or loose crosslinking reactions with the urethane groups and other reactions, such as crosslinking or curing with polyvalent metals and other materials (such as ammonium dichromate), and for interaction with functional groups carried on various substrates contacted by the polymers. Aside from their reactivity, the carboxy groups provide for excellent adhesion to a variety of substrates, especially if curing agents, such as those mentioned, are used with the polyurethanes.

The polyurethane intermediates carrying ester groups, the saponified forms or the free carboxyl resins of the present invention because of their unique physical properties may advantageously be used as burn dressings. The polyurethane resin may be applied to the burn as a powder, film, or from solution in a volatile non-toxic solvent and will form a barrier that is permeable to liquids. Thus the physician has a choice of medication which may be applied to the burn prior to the resin coating or the medication may be added to the resin for timed release. A particularly advantageous burn dressing is a powder obtained by the low temperature grinding of from about 1 to about 80 parts by weight of the polyurethane resins in their carboxyl forms and a high-boiling, water soluble non-toxic solvent for the polymer, such as glycerol, dimethylsulfoxide or low molecular weight polyethylene glycols.

The above described polyurethane resins are also useful as coatings, molding compounds, absorbents, controlled release agents, ion exchange resins, in the repair of skin abrasions and in the manufacture of dialysis membranes, denture liners, cannulae, contact lenses, solubilizing packaging components, hair sprays, cosmetics, burn dressings, contraceptive devices, sutures, surgical implants, blood oxygenators, intrauterine devices, vascular prostheses, perfume fixatives, dedorant compositions, antifog coatings, surgical drapes, oxygen exchange membranes, artificial fingernails, finger cots, adhesives, gas permeable membranes, and in protective and drag resistant coatings for boat hulls and fluid conduits of all kinds.

The invention is further illustrated by the following non-limiting examples in which all parts and percentages are by weight unless otherwise indicated.

Example 1 illustrates the ease with which polyurethanes of the invention can be handled due to the difference in solubility of salt and acid forms of the polymers, the former being water soluble but the latter becoming water insoluble. If ammonia or other fugitive monovalent salt-forming compound is used for neutralization of the carboxylic groups, the water-soluble resin becomes water-insoluble after drying and removal of ammonia. Addition of amino compounds of low volatility such as di- and tri-ethanolamines, morpholine, and the like is useful because such compounds remain in the film after the water has vaporized and thereby improves film continuity.

Example 2 describes a polyurethane especially adapted for drug delivery and sustained release. The carboxy groups provide adhesion to the stomach mucosa and thus prolong the dwell time in the stomach of a composition based on the polyurethane carrying medication (capsule, coated tablet, etc.).

Examples 3-5 illustrate polyurethanes which are particularly suitable as permanent coatings for boat hulls, such coatings usually being cured by the action of light on compositions containing ammonium dichromate. The coatings lower hydrodynamic drag and thus allow increase in vessel speed at the same engine output or allow lowering of engine output for the same speed.

Example 6 illustrates the versatility of the polyurethanes as hard, high adhesion coatings (for example, for use in fingernail polishes) due to solubility in a host of solvents both polar and non-polar.

EXAMPLE 1

In forming the ester reactants of the invention, it is convenient to use alcohols with four or more carbon atoms, because these have a limited water solubility and the reaction can be run in an excess of alcohols under refluxing conditions, the reflux condensate going through a device which will separate the water and return the alcohol to the reaction (similar to Dean-Stark trap). If lower alcohols are used, a fractionating column is required. Any conventional esterification catalyst may be used, such as toluene sulfonic acid, inorganic acids, ion exchange resins, sodium alcoholates, etc. A preferred catalyst is tetrabutyl titanate and a typical esterification formulation is the following:

| | |
|---|---|
| malic acid (hydroxy succinic acid) | 134.6 parts |
| n-butanol | 205.2 parts |
| tetrabutyl titanate | 0.2 parts |

These reagents are mixed in a reaction vessel equipped with a stirrer and a reflux condenser having a Dean-Stark trap. After refluxing the mixture for 8 hours, 26.6 parts of water are collected. The acid value is 20.6. Then 30 parts of n-butanol are added with 0.1 parts of tetrabutyl titanate and the refluxing continued for another three hours. A total of 31.8 parts of water is collected to this point and the final acid value is 8.3. The resulting ester is used to prepare a hydrophilic polyurethane resin as follows.

A mixture of 60.1 parts of CARBOWAX ® 1450 (a polyethylene glycol having a number average molecular weight of 1450, Union Carbide Corporation), 1.7 parts of glycerol and 25.5 parts of DESMODUR W ® [methylene-bis(cyclohexyl-4-isocyanate), Mobay Chemical Corp.] is prepared and incrementally reacted by heating at 65° C. for 44 minutes, catalyzed by 0.2 parts of stannous octoate (T-9, Air Products and Chemicals Co.). At the end of this period, 40% of the isocyanate has reacted. Two more short exposures (12 minutes each) to 40° C. bring the amount of reacted isocyanate to 50.0%. The reaction mixture becomes very viscous and tetrahydrofurane solvent is added in sufficient quantity to reduce the viscosity.

At this point, 29 parts of the aforesaid n-butyl ester of malic acid are added with an additional 0.1 part of stannous octoate. The temperature is brought to 55°-60° C. for a period of 1.5 hours. At the end of this period, the isocyanate is found to be completely reacted.

The reacted resin is mixed with double the amount of sodium hydroxide stoichiometrically required to saponify the ester. An additional 18.3 parts of 50% NaOH are mixed well with the resin solution which is then held for 24 hours at room temperature to complete the reaction. A fine precipitate of sodium carbonate forms during this time. The solution is neutralized with 10% hydrochloric acid and becomes clear at pH 5.0. The final pH is 3.0.

The resin obtained after evaporating the solvent is insoluble in water, but dissolves to a slightly turbid solution in water containing ammonium hydroxide (about 3.5% $NH_3$). This ammoniated solution dries to a clear film which is not water soluble but is soluble in lower aliphatic alcohols and other suitable solvents.

EXAMPLE 2

A hydrophilic resin is made, using the following formulation:
68.1 parts CARBOWAX 1450
9.7 parts diethylene glycol
0.5 parts water
40.9 parts dibutyl ester of tartaric acid
80.8 parts DESMODUR W
0.4 parts stannous octoate.

The isocyanate is placed in a reaction vessel with 0.15 parts of the stannous octoate. The dibutyl ester of tartaric acid is then added in increments of approximately 2 parts each. Temperature of the reaction is maintained at 60°-75° C. by supplying heat or delaying the next addition of the ester. The ester is added during a one hour period, at the end of which time the mass becomes so viscous that it can no longer be stirred. Tetrahydrofuran solvent is added to reduce the viscosity.

The balance of the molten polyglycols and the rest of the catalyst is added to the batch. After heating and vigorous mixing, the mass becomes homogeneous and is poured into a polypropylene tray and placed into an oven at 100° C. to cure. Before placing into the oven, 81.1% of the isocyanate is found to be reacted. After two hours of heating, the percent of reacted isocyanate rises to 97%, and an additional hour at 120° C. brings it to 98.3%.

The resin thus produced contains butyl ester groups, which alter the mechanical and the surface properties of the polymer. Saponification of the ester is accomplished in solution by adding between 1.05 and 1.10 equivalent of sodium hydroxide (as a 20% solution in water) per ester group, and heating the solution to the refluxing temperature of the solvent for several hours. The sodium salt of the carboxylic acid is formed and n-butanol is liberated.

EXAMPLE 3

52.4 parts of CARBOWAX 1450 are heated with 8.9 parts of diethylene glycol, 0.24 parts of water and 1.5 parts of diethyl ester of tartaric acid (Fluka Chemical Corp., Hauppauge, N.Y.) until the CARBOWAX diol melts and a homogeneous mixture is obtained. 37.0 parts of DESMODUR W are added and mixed with the glycols, bringing the temperature of the mixture to about 50° C. At this stage, 0.15 parts of stannous octoate are added under vigorous mixing. The reaction mixture starts to exotherm in about 1.5 minutes. When the temperature reaches 70° C., the reaction mixture is quickly poured into a polyethylene tray and placed in an oven, where it is cured for 1.5 hours at 100° C.

For the saponification of the ethyl ester of the tartaric acid in the resin, 2N solution of sodium hydroxide is used in a 5% excess of the equivalent of the ester groups. This is effected by dissolving the resin in methyl alcohol to 20% solids, adding the proper amount of the sodium hydroxide solution and stirring the mixture under nitrogen (to remove carbon dioxide and prevent formation of sodium carbonate) for 12 hours at slightly elevated temperature (25°-30°). The viscosity of the saponified solution is much less than the solution of the resin in the ester form.

The resulting carboxylate form of the resin is neutralized from pH 10 to about pH 6 with a diluted solution of hydrochloric acid. This converts most of the sodium salt groups to carboxylic acid groups.

EXAMPLE 4

52.5 parts of CARBOWAX 1450, 8.9 parts of diethylene glycol, 0.2 parts of water and 1.9 parts of dibutyl ester of tartaric acid (Fluka Chemical Corporation) are reacted with 36.4 parts of DESMODUR W essentially as described in Example 3. The resulting resin is 99.2% reacted after the oven curing.

The resin is dissolved to 20% solids in methyl alcohol, and the butyl ester groups are saponified using 2N sodium hydroxide, as described in Example 3. The viscosity of the resin solution in ester form is 925 cP (at 25° C.) and the viscosity of the resin in the carboxy form is 44 cP (at 25° C.).

When films are cast from the resin solutions, dired and then hydrated, it is found that the ester form of the polyurethane has an equilibrium water content of 58.0% and expansion of 42.1%, while the sodium salt (carboxylate) form has an equilibrium water content of 64.5% and expansion of 51.7% on swelling. The tensile strength of the ester form material is 2500 psi dry and 2396 psi wet, while the carboxylate form material has a tensile strength of 790 psi dry and 567 psi wet. On the other hand, the modulus at 100% elongation is 198 psi dry and 173 psi wet for the ester form material, and 538 psi dry and 263 psi wet for the carboxylate form material, showing increased stiffness in the latter form.

EXAMPLE 5

Because the reactivity of the ester reactants is somewhat lower than that of the polyols, a prepolymer method of preparation may be utilized as follows. 36.4 parts of DESMODUR W, and 1.9 parts of dibutyl ester of tartaric acid are placed in a reaction vessel with 0.2 parts of stannous octoate and heated to 40° C. for 30 minutes. This prepolymer is mixed with a glycol component (preheated to 53° C.) consisting of 52.5 parts of CARBOWAX 1450, 8.9 parts of diethylene glycol and 0.2 parts of water. Polyurethane formation takes place and the resin is cured at 100° C. for 1.5 hours. The resulting resin is found to be 99.95% reacted.

EXAMPLE 6

The physical properties of urethane resins can be altered by the ester reactants, particularly by dihydroxy dicarboxy acid esters, when preparing the polyurethanes of the invention. Conventional hydrophilic polyurethanes are generally very polar and therefore are soluble in polar solvents such as alcohols, dimethyl formamide and tetrahydrofuran, but are poorly soluble in less polar solvents such as aromatic solvents and esters and are partially soluble in ketone/alcohol mixtures. The addition of carboxy groups to the polyurethane resin in the manner of the invention, however, reduces the overall cohesive energy and density of the resin and results in increased solubility of the polymers in even the less polar solvents. This is demonstrated as follows.

A suitable non-polar solvent, such as toluene or ethyl acetate, is placed in a reaction vessel equipped with stirrer, refluxing condenser and an adding vessel. 29.6 parts of dibutyl ester of tartaric acid, 12 parts of diethylene glycol and 0.2 parts of stannous octoate are then dissolved in the solvent at temperatures ranging between 70° and 80° C. The amount of the solvent is calculated to be between 70-75% of the final mixture (25-30% solids based on the finished resin).

58.4 parts of DESMODUR W are then added dropwise to the stirred reaction mixture at a rate which does not cause the temperature to overshoot the chosen range. The mixture is stirred at the chosen temperature for another two hours after addition of the DESMODUR W is completed and remains liquid. The product is useful in a fingernail polish. A polyurethane prepared essentially as described but without the tartaric acid ester forms a solid product unless the reaction is conducted in a polar solvent medium, e.g., dimethyl formamide.

We claim:
1. A hydrophilic polyurethane ester intermediate consisting essentially of the reaction product of
(A) a polyol component comprising at least one of
   (a) an alkylene glycol,
   (b) a long chain polyoxyalkylene glycol, and
   (c) a linear polyester diol derived from the condensation of one or more diols with one or more dibasic acids;
(B) a carboxylic acid ester component comprising at least one of

(a) a hydroxy carboxylic acid ester selected from at least one of

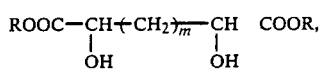

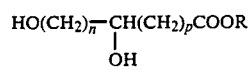

and

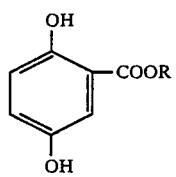

wherein R is an aliphatic group, m and p independently are integers of from 0 to 12, and n is an integer of from 1 to 12; and
(b) an amino acid ester having at least two active hydrogen atoms; and
(C) an organic isocyanate or isocyanate precursor containing at least two NCO groups;
the ratio of NCO to active hydrogen atoms in the reaction mixture being from 0.5/1 to 1/1.

2. The hydrophilic polyurethane intermediate of claim 1 wherein the carboxylic acid ester component (B) reacted with said polyol component (A) comprises at least one of said hydroxy carboxylic acid esters (a).

3. The hydrophilic polyurethane intermediate of claim 1 wherein the carboxylic acid ester component (B) comprises at least one of said amino acid esters (b).

4. The hydrophilic polyurethane intermediate of claim 2 wherein said polyol component (A) reacted with said carboxylic acid ester comprises at least one of said alkylene glycols (a) and said long chain polyoxyalkylene glycols (b).

5. The hydrophilic polyurethane intermediate of claim 4 wherein said alkylene glycols (a) are selected from one or a mixture of ethylene glycol and diethylene glycol.

6. The hydrophilic polyurethane intermediate of claim 2 wherein said polyol component (A) comprises a polyoxyethylene glycol and said organic polyisocynate (C) comprises methylene bis(cyclohexyl-4,4-isocyanate).

7. The hydrophilic polyurethane intermediate of claim 2 wherein said polyol component (A) comprises diethylene glycol and a polyoxyethylene glycol, and said organic diisocyanate (C) comprises methylene bis(-cyclohexyl-4-isocyanate).

8. The hydrophilic polyurethane intermediate of claim 2 wherein the carboxylic acid ester component (B) comprises a butyl ester of malic acid.

9. The hydrophilic polyurethane intermediate of claim 2 wherein the carboxylic acid ester component (B) comprises a dibutyl ester of tartaric acid.

10. The hydrophilic polyurethane intermediate of claim 2 wherein the carboxylic acid ester component (B) comprises a diethyl ester of tartaric acid.

11. A hydrophilic polyurethane prepared by saponifying the intermediate of claim 1.

12. A hydrophilic polyurethane prepared by saponifying the intermediate of claim 2.

13. A hydrophilic polyurethane prepared by saponifying the intermediate of claim 3.

14. A hydrophilic polyurethane prepared by saponifying the intermediate of claim 4.

15. A hydrophilic polyurethane prepared by saponifying the intermediate of claim 5.

16. A hydrophilic polyurethane prepared by saponifying the intermediate of claim 6.

17. A hydrophilic polyurethane prepared by saponifying the intermediate of claim 7.

18. A hydrophilic polyurethane prepared by saponifying the intermediate of claim 8.

19. A hydrophilic polyurethane prepared by saponifying the intermediate of claim 9.

20. A hydrophilic polyurethane prepared by saponifying the intermediate of claim 10.

21. A hydrophilic polyurethane prepared by saponifying and then neutralizing the intermediate of claim 1.

22. A hydrophilic polyurethane prepared by saponifying and then neutralizing the intermediate of claim 2.

23. A hydrophilic polyurethane prepared by saponifying and then neutralizing the intermediate of claim 4.

24. A hydrophilic polyurethane prepared by saponifying and then neutralizing the intermediate of claim 7.

25. A hydrophilic polyurethane prepared by saponifying and then neutralizing the intermediate of claim 8.

26. A hydrophilic polyurethane prepared by saponifying and then neutralizing the intermediate of claim 9.

27. A hydrophilic polyurethane prepared by saponifying and then neutralizing the intermediate of claim 10.

28. An article of manufacture comprising a shaped body formed of the hydrophilic polyurethane of claim 11.

29. The article of claim 28 wherein the shaped body is a film.

30. The article of claim 28 wherein the shaped body is a catheter.

31. An article of manufacture comprising a substrate carrying a layer of the hydrophilic polyurethane of claim 11.

32. A body implant comprising the combination of a solid hydrophilic polyurethane of claim 11 and a medicament.

33. An oral delivery system comprising a pharmacologically active agent and as a carrier vehicle therefor, a hydrophilic polyurethane of claim 11.

34. A cannula, the walls of which are formed of a hydrophilic polyurethane of claim 11.

35. An article of manufacture comprising a substrate coated with the hydrophilic polyurethane of claim 11.

36. The article of claim 37 wherein the substrate is a boat hull.

37. A method of reducing hydrostatic friction on a substrate, comprising coating the substrate with the hydrophilic polyurethane of claim 11.

* * * * *